(12) United States Patent
Lee et al.

(10) Patent No.: US 7,078,222 B2
(45) Date of Patent: Jul. 18, 2006

(54) MICROORGANISM FOR PRODUCING RIBOFLAVIN AND METHOD FOR PRODUCING RIBOFLAVIN USING THE SAME

(75) Inventors: Kwang Ho Lee, Yongin (KR); Young Hoon Park, Seongnam (KR); Jong Kwon Han, Yongin (KR); Jang Hee Park, Seoul (KR); Kyung Han Lee, Yongin (KR); Hyang Choi, Anyang (KR)

(73) Assignee: CJ Corp. (KR)

( * ) Notice: Subject to any disclaimer, the term of this patent is extended or adjusted under 35 U.S.C. 154(b) by 26 days.

(21) Appl. No.: 10/454,220

(22) Filed: Jun. 4, 2003

(65) Prior Publication Data

US 2004/0110248 A1    Jun. 10, 2004

(30) Foreign Application Priority Data

Dec. 5, 2002    (KR) .................. 10-2002-0076867

(51) Int. Cl.
C12N 1/20 (2006.01)
C12P 25/00 (2006.01)

(52) U.S. Cl. .................... 435/252.5; 435/66
(58) Field of Classification Search .............. 435/252.5
See application file for complete search history.

(56) References Cited

U.S. PATENT DOCUMENTS 5,231,007 A    7/1993    Heefner et al. ............... 435/66
5,837,528 A    11/1998   Perkins et al. .......... 435/252.31

FOREIGN PATENT DOCUMENTS

| DE | 198 40 709 A1 | 6/1999 |
|---|---|---|
| EP | 0 405 370 A1 | 1/1991 |
| EP | 0 531 708 A2 | 3/1993 |
| EP | 0 821 063 A2 | 1/1998 |
| EP | 1 186 664 A2 | 3/2002 |
| FR | 2.204.687 | 5/1974 |
| JP | 49-66894 | 6/1974 |
| JP | 03-117489 | 5/1991 |
| JP | 05-064597 | 3/1993 |
| JP | 10-084978 | 4/1998 |
| JP | 11-243976 | 9/1999 |
| WO | WO 95/26406 | 10/1995 |

OTHER PUBLICATIONS

Holtzclaw et al., J. Gen. Microbiol., 88 (2): 289-294, 1975.*
"Genetic engineering of *Bacillus subtilis* for the commercial production of riboflavin"; Authors: J.B. Perkins, A. Sloma, T. Hernamm, K. Theriault, E. Zachgo, T. Erdenberger, N. Hannett, N.P. Chatterjee, V. Williams, II, G.A. Rufo, Jr., R. Hatch and J. Pero; Journal of Industrial Microbiology & Biotechnology, 22 ; Society for Industrial Microbiology; pp. 8-18; 1999.
The Merck Index, Merck & Co.; pp. 1183, 1184; 1983.
"Threonine Aldolase Overexpression plus Threonine Supplementation Enhanced Riboflavin Production in *Ashbya gossypii*"; Authors: Nicole Monschau, Hermann Sahm adn K.-Peter Stahmann; Applied and Environmental Microbiology; American Society for Microbiology; vol. 64, No. 11; pp. 4283-4290; Nov. 1998.
"Micorbial Production of Riboflavin Using Riboflavin Overproducers, *Ashbya gossypii, Bacillus subtilis, and Candida famate*: An Overview"; Authors: Seong Han Lim, Jong Soo Choi, and Enoch Y. Park; Biotechnol. Bioprocess Eng., vol. 6, No. 2; pp. 75-88; 2001.
European Search Report; Ref. DK/CJ/G21077EP; Application No. 03253626.0-1212-; Mailing date of Aug. 12, 2003.
Japanese Office Action of Japanese Patent Application No. 2003-142491; Mailed: Mar. 28, 2006.

* cited by examiner

*Primary Examiner*—Nancy Vogel
(74) *Attorney, Agent, or Firm*—Cantor Colburn LLP

(57) ABSTRACT

Riboflavin-producing *Bacillus subtilis* which is resistant to threonine analogue, and a method for producing riboflavin using the *Bacillus subtilis* are provided.

The subject *Bacillus subtilis* referred to as *Bacillus subtilis* CJKB0002 has the accession number KCCM-10446, having been deposited in Korean Culture Center of Microorganisms (KCCM), 361-221, Yurim B/D, Hongie-1-dong, Seodaemun-gut, Seoul 120-091 Republic of Korea, on Nov. 18, 2002.

10 Claims, No Drawings

MICROORGANISM FOR PRODUCING RIBOFLAVIN AND METHOD FOR PRODUCING RIBOFLAVIN USING THE SAME

BACKGROUND OF THE INVENTION

This U.S. non-provisional application claims priority under 35 U.S.C. §119 to Korean Patent Application No. 2002-76867, filed on Dec. 5, 2002, in the Korean Intellectual Property Office, the contents of which are incorporated herein by reference in its entirety

1. Field of the Invention

The present invention relates to a microorganism for producing riboflavin and a method for producing riboflavin using the same. More particularly, the present invention relates to a mutant of *Bacillus subtilis* with enhanced riboflavin productivity, when compared to the parent strain, and a method for producing riboflavin using the same.

2. Description of the Related Art

Riboflavin, also known as vitamin B2, is a water-soluble vitamin that is manufactured by biosynthesis of various microorganisms and plants. However, riboflavin cannot be biosynthesized in vertebrate including humans. Riboflavin is a precursor for flavin adenine dinucleotide (FAD) and flavin mononucleotide (FMN), coenzymes involved in the oxidation-reduction reactions of all cellular bodies, and thus is an essential nutrient for animals including humans. Deficiency of riboflavin may result in inflammation of the mouth and the mucous membrane of the pharynx, skin inflammation and other skin injuries, conjunctivitis, amblyopia, growth inhibition, and weight loss. Therefore, riboflavin is used as a vitamin product for prevention or treatment of diseases associated with the aforementioned vitamin deficiency or as a feed additive for raising livestock. In particular, concentrated riboflavin has been used as a feed by itself. The current worldwide production of riboflavin is 3,000 tones per year, of which 75% is used for feed additives and the remainder is used for food and pharmaceuticals.

Presently, riboflavin is produced by chemical synthesis or by fermenting microorganisms. In the chemical synthesis, highly pure riboflavin is produced by a multi-step process using a precursor such as D-ribose. However, due to a high cost of the starting material, the production cost is also high for chemical synthesis. Therefore, fermentation process of riboflavin by microorganisms was developed. Microorganisms for the fermentation process may be any riboflavin-producing microorganisms that exist in nature or riboflavin-overproducing microorganisms that are transformed by a genetic engineering, chemical, or physical process. These microorganisms are cultured under an appropriate condition to produce riboflavin. The produced riboflavin is recovered from the culture.

Microorganisms widely known for riboflavin production are *Saccharomyces* sp. and *Candida* sp. belonging in the yeast group, *Clostridium* sp., *Bacillus* sp., and *Corynebacterium* sp. belonging in the bacteria group, and *Eremothecium* sp. and *Ashbya* sp. belonging in the fungi group.

U.S. Pat. No. 5,231,007 discloses a method for producing riboflavin using *Candida famata* yeast. It was reported that genetically engineered *Bacillus subtilis* and *Corynebacterium ammoniagenes* which overexpress the genes of the enzymes involved in riboflavin biosynthesis produced riboflavin of 4.5 g/l and 17.4 g/l, respectively [Perkins et al., *J. Ind. Microbiol. Biotechnol.*, 22:8–18, 1999]. European Patent No. EP 0 821 063 discloses a method for producing riboflavin using a recombinant *Bacillus subtilis*. U.S. Pat. No. 5,837,528 discloses a recombinant strain of *Bacillus subtilis* for overproducing riboflavin obtained by introducing the rib operon into the parent strain using a recombinant technology. In addition, there are *Eremothecium ashbyii* and *Ashbya gossypii* ascomycete fungi which were reported by Windholz et al. [The Merck Index, Merck & Co., p.1183, 1983] as microorganisms for riboflavin production. In particular, it was reported that culture of mutants of these ascomycete fungi in nutrient media containing molasses or vegetable oil as a main carbon source resulted in 15 g of riboflavin per 1 liter of a fermentation solution [Bigelis, *Biotechnology*, vol.7b, p.243, 1989]. Production of riboflavin using *Ashbya gossypii* is also disclosed in WO95/26406.

However, development of microorganisms with enhanced riboflavin productivity for mass-production of riboflavin is still in need.

Meanwhile, it is reported that deregulation of aspartokinse, a main enzyme of threonine biosynthesis may be closely connected with biosynthesis of riboflavin [Stahmann et al., *Applied and Environmental Microbiology*, 4283–4290, 1998].

However, until now, there have been no detailed reports about correlation between riboflavin biosynthesis pathway and threonine biosynthesis pathway. There have been also no reports that threonine resistance is introduced to riboflavin-producing strains to enhance productivity of riboflavin.

SUMMARY OF THE INVENTION

The present invention provides riboflavin-producing *Bacillus subtilis* which is resistant to threonine analogue.

The present invention also provides a method for producing riboflavin using the *Bacillus subtilis*.

According to an aspect of the present invention, there is provided riboflavin-producing *Bacillus subtilis* which is resistant to threonine analogue. Preferably, *Bacillus subtilis* CJKB0002 is used (accession number: KCCM-10446).

While searching for microorganisms with enhanced riboflavin productivity, the present inventors found that inducing mutation on *Bacillus subtilis* and introducing threonine analogue resistance to it result in the enhancement of productivity of riboflavin. Among these strains, the present inventors selected riboflavin-overproducing and high yielding strains and produced riboflavin in large scale using the selected strains.

According to another aspect of the present invention, there is provided a method for producing riboflavin comprising culturing the *Bacillus subtilis* and recovering riboflavin from the culture.

DETAILED DESCRIPTION OF THE INVENTION

Hereinafter, the present invention will be described in detail.

The *Bacillus subtilis* of the present invention is a mutant of *Bacillus subtilis* AS5 (BIONOM-S, Ltd., Russia). It is threonine analogue resistant and produces high concentration of riboflavin in high yield.

The parent strain as used herein is *Bacillus subtilis* AS5 (BIONOM-S, Moscow, Russia).

Conventional physical or chemical processes can induce mutation on the parent strain. For example, the parent strain may be exposed to X-rays or UV light, or a chemical agent such as N-methyl-N'-nitro-N-nitrosoguanidine (NTG), diethylsulfate, and ethylamine.

The present inventors cultured mutation-induced strains in media containing various concentrations of DL-β-hydroxynorvaline as threonine analogue. Mutants capable of growing in the presence of a high concentration of DL-β-hydroxynorvaline were selected. Among them, one mutant with the highest riboflavin productivity was selected. The selected mutant was designated as *Bacillus subtilis* CJKB0002 and deposited in the Korean Culture Center of Microorganisms on Nov. 18, 2002 (accession number: KCCM-10446).

The *Bacillus subtilis* CJKB0002 (KCCM-10446) of the present invention can grow in even up to a 250 mg/l of DL-β-hydroxynorvaline-containing medium. On the other hand, the *Bacillus subtilis* AS5 as the parent strain cannot grow in the presence of more than 50 mg/l of DL-β-hydroxynorvaline.

In addition, in flask culture, the productivity of riboflavin of the *Bacillus subtilis* CJKB0002 (KCCM-10446) of the present invention is 13% higher than that of the *Bacillus subtilis* AS5. In 5-liter fermenter culture, the *Bacillus subtilis* CJKB0002 (KCCM-10446) produces riboflavin at an increased level of 18.4%, when compared to the *Bacillus subtilis* AS5.

Therefore, the *Bacillus subtilis* CJKB0002 (KCCM-10446) of the present invention has five times enhanced resistance to threonine analogue and substantially enhanced riboflavin productivity, when compared to the *Bacillus subtilis* AS5.

In order to produce riboflavin, the *Bacillus subtilis* CJKB0002 (KCCM-10446) of the present invention is cultured under a suitable condition.

In detail, the *Bacillus subtilis* CJKB0002 (KCCM-10446) is inoculated onto a conventional medium containing a suitable carbon source, nitrogen source, and inorganic compounds and cultured at a predetermined temperature and pH under an aerobic condition. Examples of the carbon source include glucose, molasses, lactose, sucrose, maltose, dextrin, starch, mannitol, sorbitol, and glycerol. Preferably, glucose and molasses are chosen. Examples of the nitrogen source include an inorganic source such as ammonia, ammonium chloride, and ammonium sulfate and an organic source such as peptone, NZ-amine, beef extract, yeast extract, corn steep liquor, casein hydrolysate, fish or fish meal, and defatted soybean cake or meal. Preferably, yeast extract and corn steep liquor are chosen. Examples of the inorganic compounds include potassium monohydrogen phosphate, potassium dihydrogen phosphate, magnesium sulfate, ferrous sulfate, manganese sulfate, and calcium carbonate. When needed, vitamins and auxotrophic bases may be used. For the culture, shaking culture or stirring culture by aeration may be used. The culture temperature ranges from 30 to 45° C., and preferably 37 to 40° C. During the culture, it is preferable that the pH is adjusted to a fairly neutral level. The culture period is 5 to 6 days.

According to one embodiment of the present invention, the *Bacillus subtilis* CJKB0002 (KCCM-10446) was inoculated onto a seed medium and cultured at an aeration flow rate of 1 vvm, 37° C., and 8,000 rpm for 20 hours. The seed culture was inoculated onto a fermentation medium and was subjected to shaking culture at an aeration flow rate of vvm, 40° C., 800 rpm, and pH 7.0 for 60 to 70 hours. During the shaking culture, the fermentation culture was supplied with a glucose supplement medium to maintain the residual glucose in the culture to a level of 0.5 to 1% until the total content of glucose in the fermentation culture reached 20%. Riboflavin was yielded at an increased level of about 18.4%, when compared to the parent strain.

Hereinafter, the present invention will be described more specifically by examples. However, the following examples are provided only for illustrations and thus the present invention is not limited to or by them.

EXAMPLE 1

Selection of *Bacillus subtilis* CJKB0002 of the Present Invention

In order to obtain the *Bacillus subtilis* CJKB0002 of the present invention, the *Bacillus subtilis* AS5 as the parent strain was subjected to mutation. Then, the mutants of the *Bacillus subtilis* AS5 were cultured in DL-β-hydroxynorvaline-containing media to obtain colonies. Among these colonies, a mutant strain with the highest riboflavin productivity was selected as the *Bacillus subtilis* CJKB0002.

The *Bacillus subtilis* AS5 as the parent strain was obtained from BIONOM-S, Ltd. (Obolensk, Moscow, Russia). The *Bacillus subtilis* AS5 was suspended in phosphate buffer at pH 7.0 or citrate buffer at pH 5.5 to have a cell density of $10^7$ to $10^8$ cells/ml. A mutation-inducing agent, N-methyl-N'-nitro-N-nitrosoguanidine was added to the suspension until its concentration was 10 to 50 μg/ml. The resultant mixture was incubated at room temperature or 30° C. for 30 to 60 minutes to induce mutation. Then, the mixture was washed three times with 0.85% of saline solution and diluted in an appropriate manner. The diluted solution was plated onto 1.8% agar-containing minimal media with various concentrations of DL-β-hydroxynorvaline and cultured at 37° C. for 24 hours to obtain colonies. In this case, the concentration of DL-β-hydroxynorvaline ranged from 0 mg/l to 350 mg/l. The formed colonies were inoculated onto nutrient media and cultured at 37° C. for 24 hours. Then, the resultant nutrient cultures were inoculated onto fermentation media and cultured at 37° C. for 4 to 5 days. The highest riboflavin-producing strain was selected. Each medium composition is presented in Table 1.

TABLE 1

Compositions of media for selection of *Bacillus subtilis* CJKB0002 of the present invention

| Medium | Composition |
| --- | --- |
| Nutrient medium | 10 g/l of tryptose, 3 g/l of beef extract, 5 g/l of sodium chloride, 15 g/l of agar, pH 7.2 |
| Minimal medium | 2.5 g/l of glucose, 7 g/l of monopotassium phosphate, 3 g/l of dipotassium phosphate, 0.5 g/l of sodium citrate, 0.75 g/l of magnesium sulfate 7-hydrate, 0.5 g/l of yeast extract, 0.15 g/l of casamino acid, 20 mg/l of tryptophan, pH 7.2 |

TABLE 1-continued

Compositions of media for selection of *Bacillus subtilis* CJKB0002 of the present invention

| Medium | Composition |
|---|---|
| DL-β-hydroxynorvaline-containing medium | 0 to 350 mg/l of DL-β-hydroxynorvaline + minimal medium |
| Fermentation medium | 100 g/l of glucose, 20 g/l of yeast extract, 5 g/l of corn steep liquor, 0.5 g/l of magnesium sulfate, 1.5 g/l of monopotassium phosphate, 3.5 g/l of dipotassium phosphate, 6 g/l of urea, pH 7.2 |

The productivity of riboflavin was measured by HPLC. HPLC was performed using waters 510 coupled with kromasil C18 (5 μm) column (inner diameter: 4.6 mm, length: 250 mm). A mixed solvent of 5 mM of sodium hexanesulfonate and 20 mM of $H_3PO_4$, and acetonitrile (89:11, v/v) was used as a mobile phase. The flow rate of the mobile phase was 1 ml/min. The injection amount of samples was 15 μl, and distilled water for sample dilution were used. In addition, UV detector (TSP UV2000, UV 260 nm) was used as a detector.

According to the test results, mutants which grew on 250 mg/l of DL-β-hydroxynorvaline-containing media exhibited excellent riboflavin productivity. Among them, one mutant with the highest riboflavin productivity was selected and designated as *Bacillus subtilis* CJKB0002. The *Bacillus subtilis* CJKB0002 was deposited in the Korean Culture Center of Microorganisms on Nov. 18, 2002 under accession number: KCCM-10446.

EXAMPLE 2

Evaluation of Resistance of *Bacillus subtilis* CJKB0002 and *Bacillus subtilis* AS5 Against DL-β-Hydroxynorvaline In this example, in order to evaluate resistance to DL-β-hydroxynorvaline, the *Bacillus subtilis* CJKB0002 (KCCM-10446) of Example 1 and the *Bacillus subtilis* AS5 as the parent strain were cultured in various concentrations of DL-β-hydroxynorvaline-containing media. In detail, respective strains were inoculated onto DL-β-hydroxynorvaline-containing media as shown in Table 1 and cultured at 30° C. for 5 days. In this case, the concentration of DL-β-hydroxynorvaline ranged from 0 to 350 mg/l.

According to the test results as shown in Table 2, the *Bacillus subtilis* AS5 could not grow in more than 50 mg/l of DL-β-hydroxynorvaline-containing media. On the other hand, the *Bacillus subtilis* CJKB0002 (KCCM-10446) of the present invention could grow even in a 250 mg/l of DL-β-hydroxynorvaline-containing medium.

TABLE 2

Evaluation of resistance of *Bacillus subtilis* CJKB0002 and *Bacillus subtilis* AS5 against DL-β-hydroxynorvaline

| | Concentration of DL-β-hydroxynorvaline (mg/l) | | | | | | |
|---|---|---|---|---|---|---|---|
| Strain | 0 | 50 | 100 | 200 | 250 | 300 | 350 |
| *Bacillus subtilis* AS5 | +++ | + | − | − | − | − | − |
| *Bacillus subtilis* CJKB0002 (KCCM-10446) | +++ | +++ | +++ | ++ | + | − | − |

+: growth,
−: not growth

EXAMPLE 3

Potency of Fermentation of *Bacillus subtilis* CJKB0002 of the Present Invention in Flask The potencies of fermentation of the *Bacillus subtilis* CJKB0002 and the *Bacillus subtilis* AS5 in flasks were evaluated. Each strain was inoculated onto a seed medium and cultured. Then, each seed culture was transferred to a fermentation medium in a flask. The seed medium was prepared by distributing 5 ml of a seed medium in a test tube with a diameter of 18 mm and sterilizing the test tube under pressure at 121° C. for 15 minutes. Each of the *Bacillus subtilis* CJKB0002 and the *Bacillus subtilis* AS5 was inoculated onto the seed medium and shaking culture was performed at 200 rpm and 37° C. for 20 hours. When the seed culture was completed, 1 ml of each seed culture was inoculated onto a fermentation medium in a flask and shaking culture was performed at 200 rpm and 37° C. for 90 hours. The fermentation medium was prepared by sterilizing a medium FA and a medium FS under pressure in the same manner as in the preparation of the seed medium and distributing 15 ml of the medium FA and 5 ml of the medium FS into a 250 ml shaking culture flask that was pre-sterilized under pressure. When the fermentation was completed, the concentration of riboflavin accumulated in the fermentation culture was measured in the same manner as in Example 1. Each composition of the seed medium and fermentation medium as used in this example are presented in Table 3.

TABLE 3

Compositions of media for fermentation in flask

| Medium | Composition |
|---|---|
| Seed medium | 5 g/l of yeast extract, 10 g/l of tryptone, 10 g/l of sodium chloride, No adjustment to pH |

TABLE 3-continued

Compositions of media for fermentation in flask

| Medium | Composition |
| --- | --- |
| Fermentation medium | Medium FA: 100 g/l of glucose, 20 g/l of dry yeast, 0.5 g/l of magnesium sulfate 7-hydrate<br>medium FS: 1.5 g/l of monopotassium phosphate, 3.5 g/l of dipotassium phosphate, 6 g/l of urea, pH: 7.2 to 7.4 |

According to the test results, the *Bacillus subtilis* AS5 as the parent strain produced 7.0 g/l of riboflavin. On the other hand, the *Bacillus subtilis* CJKB0002 (KCCM-10446) of the present invention produced 7.9 g/l of riboflavin, which was 13% higher than in the *Bacillus subtilis* AS5.

EXAMPLE 4

Potency of Fermentation of *Bacillus subtilis* CJKB0002 of the Present Invention in 5-liter Fermenter The potencies of fermentation of the *Bacillus subtilis* CJKB0002 (KCCM-10446) and the *Bacillus subtilis* AS5 in 5-liter fermenters were evaluated in a comparative manner. Each strain was inoculated onto a seed medium and cultured. Then, each seed culture was inoculated onto a fermentation medium and fed-batch cultured. For this, first, 1 liter of each seed medium was distributed in a laboratory fermenter with capacity of 2.5 liter and sterilized under pressure at 121° C. for 10 minutes to prepare a seed medium. After the seed medium was cooled, 10 ml of each suspension of the *Bacillus subtilis* CJKB0002 and the *Bacillus subtilis* AS5 in saline solution was inoculated onto the seed culture. Then, each strain-containing seed culture was incubated under sterile aeration at a rate of 1 vvm at 37° C. and 8000 rpm for 20 hours. During the seed culture, pH was not adjusted. After the seed culture was completed, each seed culture was inoculated onto a fermentation medium and fed-batch cultured. The fermentation medium was prepared by distributing 1.4 liter of a fermentation medium in a laboratory fermenter with capacity of 5 liter, followed by pressure sterilization at 121° C. for 20 minutes. After the fermentation medium was cooled, 200 ml of each seed culture was inoculated onto the fermentation medium and cultured under aeration at a rate of 1 vvm at 8,000 rpm and 40° C. During the fermentation, each fermentation culture was supplied with a glucose supplement medium to maintain the residual glucose in the culture to a level of 0.5 to 1% until the total content of glucose in the fermentation culture reached 20%. During the fermentation, pH was maintained to 7.0 using aqueous ammonia. The fermentation period was 60 to 70 hours.

In this example, in order to reduce production cost, molasses was substituted for glucose as a carbon source, corn steep liquor for yeast extract and tryptone as a nitrogen source, and corn steep liquor for a portion of dry yeast, both in the seed media and fermentation media. In addition, the supplement medium for the fed-batch culture contained glucose as a carbon source and dry yeast and corn steep liquor as a nitrogen source. Each composition of media as used in this example is presented in Table 4. The productivities of riboflavin in the fermentation cultures were measured in the same manner as in Example 1.

TABLE 4

Compositions of media for culture in 5-liter fermenter

| Medium | Composition |
| --- | --- |
| Seed medium | 30 g/l of molasses (50%, based on glucose), 15 g/l of corn steep liquor, 0.5 g/l of magnesium sulfate 7-hydrate, 5 g/l of ammonium sulfate, 1.5 g/l of monopotassium phosphate, 3.5 g/l of dipotassium phosphate, pH 7.4 |
| Fermentation medium | Medium FA: 20 g/l of dry yeast, 5 g/l of corn steep liquor, 2 g/l of ammonium sulfate, 0.5 g/l of magnesium sulfate 7-hydrate, 17.5 g/l of monopotassium phosphate, 7.5 g/l of dipotassium phosphate, pH 7.2–7.4<br>Supplement medium: 620 g/l of glucose, 26.7 g/l of dry yeast, 26.7 g/l of corn steep liquor |

According to the test results, the *Bacillus subtilis* AS5 as the parent strain produced 22.4 g/l of riboflavin. On the other hand, the *Bacillus subtilis* CJKB0002 (KCCM-10446) of the present invention produced 26.5 g/l of riboflavin, which was about 18.4% higher than in the *Bacillus subtilis* AS5.

As apparent from the above description, the *Bacillus subtilis* of the present invention has high resistance to threonine analogue and produces a high concentration of riboflavin in high yield. Therefore, a large amount of riboflavin can be yielded.

What is claimed is:

1. A method for producing riboflavin comprising:
   culturing a *Bacillus subtilis* strain which is resistant to threonine analogue; and
   recovering riboflavin from the culture.

2. The method of claim 1, wherein the *Bacillus subtilis* strain *Bacillus subtilis* CJKB0002 (KCCM-10446) strain.

3. A riboflavin producing *Bacillus subtilis* CJKB0002 (KCCM-10446) strain.

4. A method of producing a *Bacillus subtilis* strain with enhanced riboflavin producing ability, comprising:
   inducing a mutation in a parent *Bacillus subtilis* strain; and
   selecting a *Bacillus subtilis* mutant strain with enhanced threonine analogue resistance as compared to the parent *Bacillus subtilis* strain,
   wherein the *Bacillus subtilis* mutant strain is a *Bacillus subtilis* strain with enhanced riboflavin producing ability as compared to the parent *Bacillus subtilis* strain.

5. The method of claim 4, wherein inducing a mutation in a parent *Bacillus subtilis* strain comprises inducing the mutation in the parent *Bacillus subtilis* strain by a physical process or a chemical process.

6. The method of claim 5, wherein the physical process includes exposing the parent *Bacillus subtilis* strain to X-ray or UV light.

7. The method of claim 5, wherein the chemical process includes applying a chemical agent to the parent *Bacillus subtilis* strain.

8. The method of claim 7, wherein the chemical agent includes N-methyl-N'-nitro-N-nitrosoguanidine, diethylsulfate, or ethylamine.

9. The method of claim 4, wherein an amount of the riboflavin produced in the *Bacillus subtilis* mutant strain is at least 13% higher than an amount of the riboflavin produced in the parent *Bacillus subtilis* strain.

10. The method of claim of claim 4, wherein the *Bacillus subtilis* mutant strain is *Bacillus subtilis* CJKB0002 (KCCM-10446) strain.

* * * * *